United States Patent [19]

Panetti

[11] Patent Number: 5,020,371

[45] Date of Patent: Jun. 4, 1991

[54] DEVICE FOR THE PRECISE TRANSVERSE POSITIONING FOR A MEMBER DISPLACEABLE ALONG A RAIL OF A RAILWAY TRACK WITH RESPECT TO SAID RAIL

[75] Inventor: Romolo Panetti, Geneva, Switzerland

[73] Assignee: Speno International S.A., Geneva, Switzerland

[21] Appl. No.: 420,463

[22] Filed: Oct. 12, 1989

[30] Foreign Application Priority Data

Dec. 19, 1988 [CH] Switzerland .................. 4677/88

[51] Int. Cl.$^5$ ............................................. G01N 29/04
[52] U.S. Cl. ..................................................... 73/636
[58] Field of Search ................. 73/636, 634, 639, 597

[56]   References Cited

U.S. PATENT DOCUMENTS

| 4,044,594 | 8/1977 | Owens et al. | 73/634 |
| 4,235,112 | 11/1980 | Kaiser | 73/634 |
| 4,662,224 | 5/1987 | Turbe | 73/636 |
| 4,700,574 | 10/1987 | Turbe | 73/636 |

FOREIGN PATENT DOCUMENTS

| 0160591 | 11/1985 | European Pat. Off. . | |
| 2722961 | 11/1978 | Fed. Rep. of Germany | 73/634 |
| 3227130 | 2/1983 | Fed. Rep. of Germany . | |
| 2391470 | 12/1973 | France . | |
| 2199887 | 4/1974 | France . | |
| 941457 | 11/1963 | United Kingdom | 73/636 |

Primary Examiner—John E. Chapman
Assistant Examiner—Louis M. Arana
Attorney, Agent, or Firm—Young & Thompson

[57]   ABSTRACT

The invention relates to a method for positioning with precision a member displaced along a rail transversely with respect to the symmetry axis of the head of the rail. According to this method, one emits through the head of the rail two ultrasound beams which are practically perpendicular to the fish plates of this rail. One receives the echoes of these beams reflected by the fish plates. One forms a regulation or adjusting signal which is a function of the time difference between the emission and the reception of its echo for each of the two ultrasound beams and uses this regulating signal to elaborate a control signal for the transverse positioning of the member.

10 Claims, 3 Drawing Sheets

DEVICE FOR THE PRECISE TRANSVERSE POSITIONING FOR A MEMBER DISPLACEABLE ALONG A RAIL OF A RAILWAY TRACK WITH RESPECT TO SAID RAIL

FIELD OF THE INVENTION

The invention relates to a method and a device for the precise positioning, in a transverse direction with respect to a rail of a railroad track, of a member which is moved along said rail and particularly of a support for ultrasound transducers used for the non destructive testing of the rails.

Background of the Invention

The strains and the dynamics from the loads to which a railroad track is submitted cause the developing of internal defects in the rails, such as oval flaws, horizontal, transverse or longitudinal cracks, star flaws and so on.

It is important to be able to detect these defects on site or in the workshop through a non-destructive method, in order to change the defective rail portions.

The most used non destructive testing method of the internal state of the rails on site or in the workshop is the ultrasonic test of the rail. This technique consists in bringing emitter, receiver or emitter-receiver transducers in contact with the head of the rail, the orientation of which is adapted to the type of flaws to be detected.

The received echoes of the emitted ultrasounds are generally visualized on cathodic ray tubes. These echoes are also graphicallY plotted enabling the determination of the position and of the type of the detected flaws. The interpretation of the defects is also made by means of a digital calculator, the printer of which delivers a direct report on the place and nature of the defects.

In the case of in situ testing, the transducers can be mounted on carriages, rolling on the rails, and maintained in sonic contact with the rail through a water film. One can also use transducers located in a wheel rolling on the rail, the sonic contact between the transducer and the rolling surface being realized for example by a liquid contained in the wheel as described in U.S. Pat. No. 4,165,648.

The transducers to be used and their location are determined by the characteristics of the defects to detect. During the test it is important that each transducer remains always precisely positioned with respect to the rail of the railroad under test.

For the transducers working with a beam reflected by the sole of the rail under an angle different from zero, the longitudinal spacing of said transducers has to be a function of the height of the rail to have a good reception. For the transducers used to detect the defect in the web of the rail, which is relatively narrow, it is their transverse position with respect to the rail which has to be realized with precision.

In certain existing realizations, the lateral positioning of the transducers with respect to the rail is realized by the forced resting, through a jack or a spring, of a mechanical part rigidly connected to the transducer carrying carriage, against the lateral face of the head of the rail which is considered as a transverse geometric reference of the rail profile.

These realizations have important drawbacks related to the different width of the head of the laid rails, due to the different types of rails used as well as to the different degree of lateral wearing off or over width of the rails due to the crushing of the heads of the rails. The transducers are thus badly positioned and cannot warrant a good quality test.

There is on some realizations manual controls for the transverse or longitudinal positioning of the transducers. These devices do not give satisfaction however since these controls have to be actuated in function of a visual observation of the head of the rail, leading to an approximate result only and it is unworkable above a given speed of displacement of the testing vehicle.

The Known Prior Art

The U.S. Pat. No. 4,044,594 discloses a rail testing device by means of only one transducer located in a wheel, which necessitates a complex regulating system to correct the lateral and angular variations of the wheel resulting from irregularities of the rail surface. Such a device cannot work efficiently at relatively high speeds.

The published European patent application No. 0 160 591 discloses a method and a device for testing a rail by means of ultrasonic transducers sliding on the rail and in sonic contact with it, according to which the position of at least one of the transducers is controlled by the intensity variations of an ultrasonic beam reflected by the lower surface of the sole of the rail. According to this document it is possible to control the longitudinal as well as the transverse position of said transducer with respect to the railroad.

U.S. Pat. No. 4,235,112 discloses a laterally movable ultrasound transducer, comprising the sensor of a rail fault detection device, which is automatically centered on the rail as the detection device moves along the rail. The sensor includes a pair of ultrasound receiving transducers positioned on either side of a transducer which generates and receives ultrasonic energy. Signals provided by the receiving transducers, due to the beam of ultrasonic waves reflected by the lower face of the sole of the rail, are compared and any difference therebetween used to control the lateral position of the sensor with respect to the rail.

Therefore, the documents U.S. Pat. No. 4,044,594, U.S. Pat. No. 4,235,112 and EP 0 160 591 propose the use of the refection of one or two ultrasonic beams on the lower surface of the sole of the rail. They are based on the measurement of the intensity or of the energy of the reflected ultrasonic beams and this is not reliable. In fact the energy of these ultrasonic reflected beams is modified, perturbed by the defects present in the web of the rail and in its sole such as for example cracks or end holes. Furthermore, the lower surface of the sole of the rail is always more or less corroded and rusted, corrosion which causes also intensity modifications of the reflected ultrasonic beams. Therefore, these existing devices do not enable a precise automatic positioning of the transducers in their longitudinal or transverse optimal positions with respect to the head of the rail so that the results of the ultrasonic testing of the rails by these methods is brought with errors.

There are known from the French published patent application No 7.812.661; from the document DE-A-3.227.130 and from the French patent No 7.233.516 ultrasonic non destructing testing methods and devices for testing the longitudinal weld of tubes, or for detecting defects in machined workpieces. All these devices use the intensity of reflected ultrasound waves for the position control of the transducer and suffer thus from the afore-mentioned drawbacks. Furthermore, they use for the position control of the transducer the ultrasonic beam reflected by the outside surface of the part to be tested. This of course cannot apply to the testing of rails since the upper rolling surface of the rail to be tested is irregularly worn and can not serve as a reference surface.

There are other possible applications for which it is necessary to pOsition transversely with precision with respect to a rail a member moved along a rail track, this member carrying measuring means, testing means or reprofiling means.

For all these realizations, the present invention brings the solution to the problem encountered.

SUMMARY OF THE INVENTION

The method and the device according to the present invention remedy the precited drawbacks in that the control of the positioning, particularly of the transverse positioning, of the member moved along the rail with respect to the axis of said rail is independent of the intensity of the reflected ultrasonic beams and of the defects of the web of the rail or of the corrosion of the lower surface of the sole of the rail.

The method and the device object of the present invention are distinguished by the characteristics disclosed and claimed hereafter.

BRIEF DESCRIPTION OF THE DRAWINGS

The attached drawings shows schematically and by way of example the method and the device for positioning transversely a testing transducer of a rail of a railroad track according to the invention.

DETAILED DESCRIPTION OF THE INVENTION

Figure 1:
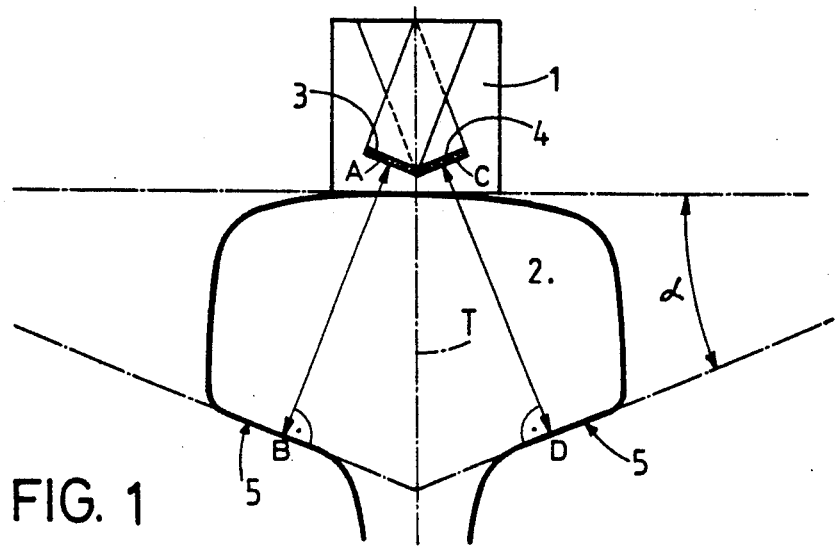
FIG. 1 shows the control transducer centered on the symmetry axis of the rail.

The present method for positioning, transversely with respect to the longitudinal axis of a rail, a member moved along said rail which carries for example ultrasonic testing transducers of said rail, comprises the assembly on a support carrying the testing transducer of the rail of a control transducer of the transverse position of said support with respect to the longitudinal axis of the rail. This control transducer is formed of two emitter-receiver transducers forming an angle between them and located in a pad sliding on the rolling surface of the rail and set in sonic contact with it for example by means of a water film. These emitter-receiver transducers each emitting a beam of intermittent ultrasounds or pulse train approximately perpendicular to each of the fish plates of the rail from which they are reflected. Then one measures the travel time of each said beam or ultrasonic pulse, i.e. in fact the distance of each said transducer to the corresponding fish plate, the transmission speed of the ultrasounds in steel being known.

The ultrasonic wave beams are constitued by pulse trains, they are thus intermittent when the member is continuously displaced along the rail. For measurement when the member stands still at different locations, on the rails, these beams could comprise only one pulse. Furthermore, these beams are synchronized, generally in such a manner that the pulses of each beam are emitted simultaneously.

Then the time interval separating a pulse of the first beam from reception of its echo is measured and is compared to the time interval between the corresponding pulse of the second beam and the reception of its echo.

One calculates then the difference between these distances, i.e. of the travelling times of these two beams, which is used to elaborate a control signal for a transverse positioning device of the transducers or of the transducer support.

In this way, one eliminates all the defects of the existing systems described in the introduction of the present patent since the measurement is independent of the energy or of the intensity of these beams and therefore of the internal defects of the rail as well as of the defects of the rail sole since said sole is no more used for the reflection of the ultrasonic beams.

This control method of the transverse position of the transducer has further the following advantages:

The ultrasound signal or beams are only very slightly damped since their travelling length in the steel is short. Only the thickness of the head of the rail is crossed and not the whole height of the rail, web included, as is the case in the existing devices.

Experience shows clearly that the fish plates have non modified surfaces since they are not subjected to wearing off nor to corrosion. The reflection on these surfaces is therefore of good quality and approximately constant at all points of the rail. Furthermore, the slope of the fish plates is practically the same whatever the type of the rail so that a same control transducer, i.e two emitter-receiver transducers forming an angle between them, can be used on any type of rail.

The centering of the transducers can be done on the symmetry axis of the rail, but also, by introducing a reference value different from zero, on straight lines extending parallel to said symmetry axis. The transducers can thus not only be positioned in the symmetry plane of the rail but also in a plane parallel to it laterally displaced and this is useful or even necessary for the testing of certain areas of the head of the rail.

The measurement being of the differenetal type it is not influenced by the absolute value of the travelling time of the ultrasound beams and is therefore completely independent from the wearing off or from the thickness of the head of the rail.

As the ultrasound beams emitted by the control transducer are slightly divergent a small variation of the angle formed by the fish plates with a plane perpendicular to the symmetry plan of the rail, i.e. parallel to its rolling surface, has no influence on the result of the measurement.

Figure 2:
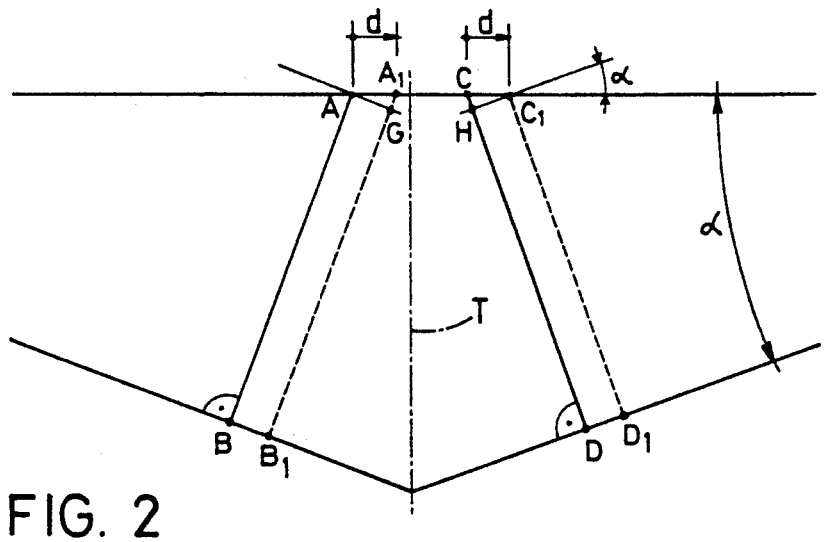
FIG. 2 shows the effect of a transverse displacement "d" with respect to the axis of the head of the rail of the control transducer.
Figure 3:
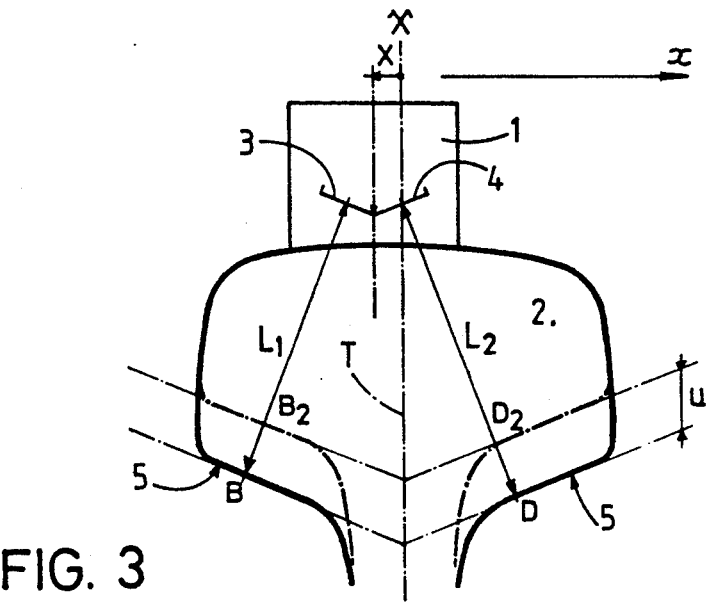
FIG. 3 shows the control transducer as being displaced of a value "X" towards the left with respect to the axis of the head of the rail.

FIGS. 1 to 3 show the principle of the positioning method which has just been described.

In FIG. 1 one sees the support 1 of the transducers sliding on the rolling table of the head 2 of the rail. This support 1 carries the control transducer formed of two emitter-receiver ultrasound transducers 3,4 which forms an angle between them pratically equal to the angle 180°—α where α is the angle formed by the fish plates 5 with the rolling table of the rail.

In this representation the support 1 and thus the control transducers 3, 4 is centered on the axis or the plane T of symmetry of the rail head 2 so that the distances, ABA on the one hand and CDC on the other hand, travelled by the beams of each of transducers 3, 4 are equal. The times taken to travel these distances are also equal and their difference is zero. In this case and provided the reference value of the position control device of the support 1 is also zero, the control signal of the device is also zero, the transducers being correctly positioned.

FIG. 2 represents the effect of a displacement of the value "d" of the support 1 parallel to the rolling surface of the rail head 2.

The distance AB becomes $A_1B_1$, that is $GB_1+GA_1$ $=AB+GA_1$ and the distance CD becomes $C_1D_1$, i.e. CD-CH where $GA_1=CH=d.\sin.\alpha$.

Thus the go and come back travel of a beam is equal to $A_1B_1+B_1A_1=2AB+2.d.\sin.\alpha$; for the other beam it is equal to $C_1D_1+D_1C_1$ i.e $2CD - 2.d.\sin.\alpha$.

The difference in length of the two paths is thus equal to:

$$\delta=2AB+2.d.\sin\alpha - (2CD - 2.d.\sin\alpha)$$

and as $AB=CD$ $$\delta=4.d.\sin\alpha$$

and the corresponding time difference is $$\Delta t=4.d.\sin\alpha/V$$

where V is the speed of the ultrasounds in steel.

It is this signal $\Delta t$ which will be compared to the reference value which is determined in this case as a function of the desired position of the support 1 to create the control signal of the positioning control device.

FIG. 3 shows the case of an excentered support 1 of a value "X" towards the left ("X" negative). In this case, L1 is smaller than L2, the difference $\delta=L1 - L2$ is negative and $\Delta t$ also. One sees thus that one knows automatically on which side of the symmetry plane T of the rail the axis of the support 1 is located due to the sign of the signal $\Delta t$ or of $\delta$.

On that figure, one sees also that a wearing off "U" of the head of the rail, reducing its thickness, is without effect on the measurement and thus on the positioning or the centering of the support 1. In fact, the travel of the first beam will be reduced by twice $BB_2$ and that of the second beam by twice $DD_2$ As the distances $BB_2$ and $DD_2$ are equal, the difference of the travels and of the travelling times of said beams remain unchanged.

Figure 7:
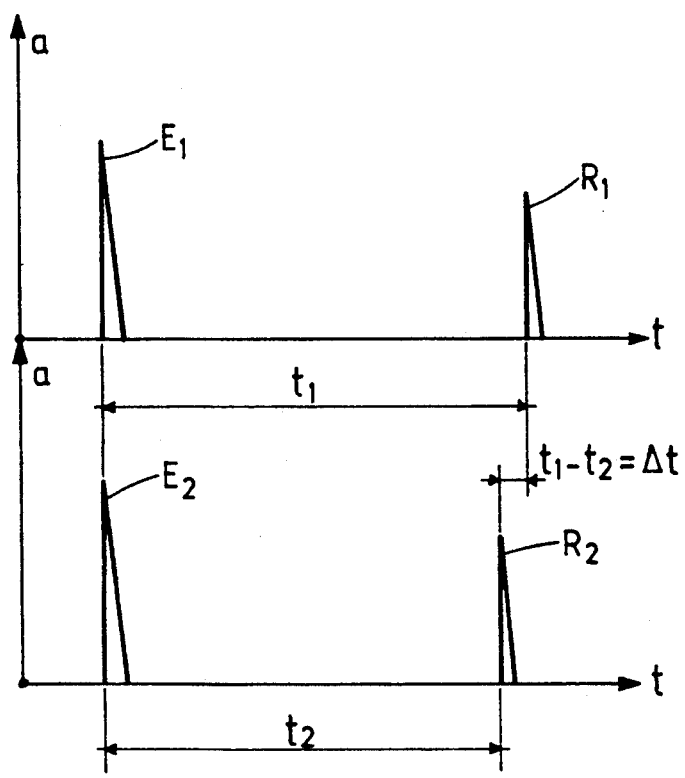
FIG. 7 is a diagram of the time "t" showing the emitted "E" and the received "R" pulses of the control transducer.

FIG. 7 is a diagram showing as a function of the time the pulses $E_1$, $E_2$ emitted by the transducers 3, 4 and their echoes $R_1$, $R_2$ received after the time $t_1$, respectively $t_2$ depending on the length of the distances $L_1$ and $L_2$.

It is evident that the energy or the intensity of the echoes R is of less amplitude than that of the emitted pulses E but this has no influence on the measurement of the times $t_1$, $t_2$ which are not bound in any way to these energy levels.

Figure 6:
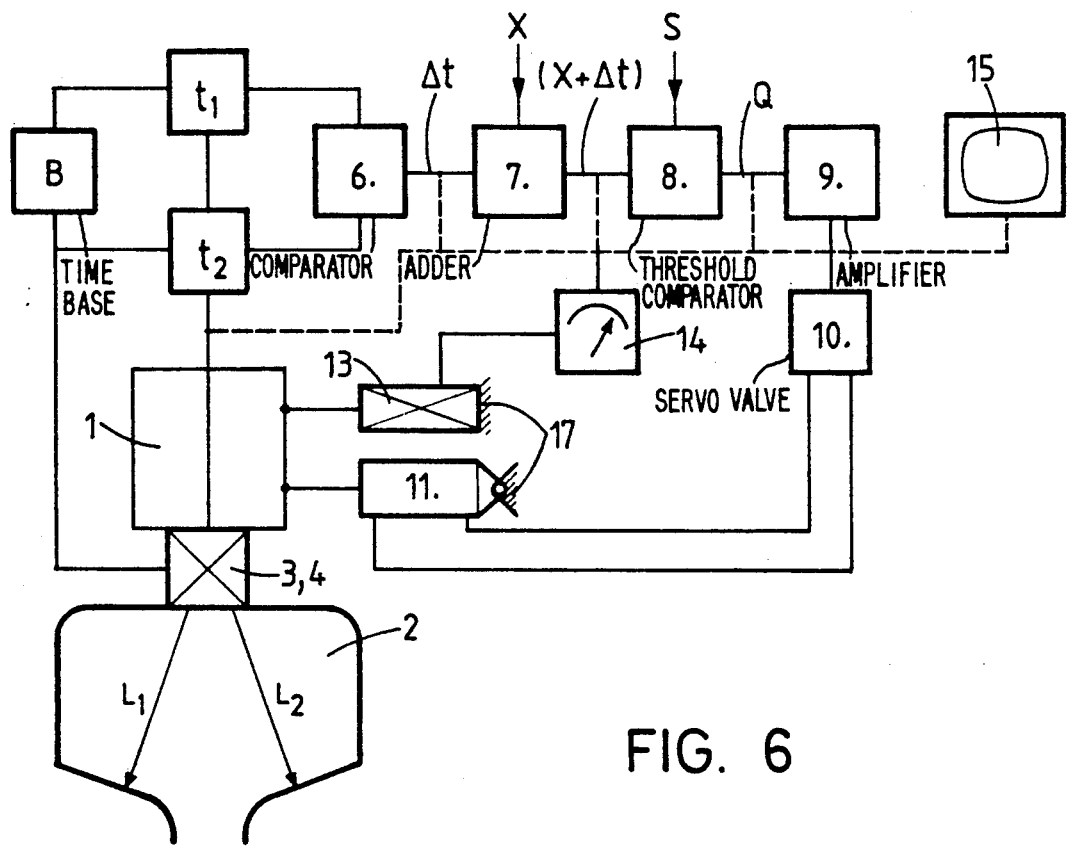
FIG. 6 shows a bloc scheme of the control device according to the invention.

FIG. 6 shows a bloc schema of the control and positioning device of a support 1 with respect to the axis of the head 2 of the rail.

The support 1 carries the control transducers 3, 4 which is in sonic contact with the rail head 2. The length $L_1$ and $L_2$ represents half the travel of the ultrasound beams emitted and received by the transducers 3,4.

This emitter-receiver control transducer 3, 4 associated with a time base B enables determining the times $t_1$, $t_2$ separating the emission of the pulses $E_1$, $E_2$ and the reception of their echoes $R_1$, $R_2$ of the transducers 3, 4. These times $t_1$, $t_2$ are compared in a comparator 6 delivering a signal $\Delta t=t_1- t_2$ This signal $\Delta t$ is added to a reference signal X through an adder 7 delivering a control signal $(X+\Delta t)$ for the positioning of the support 1. The absolute value of this control signal $(X+\Delta t)$ is compared to a threshold S in a comparator 8 delivering an adjusting signal Q only if the absolute value of the control signal is greater than the threshold S which is pre-established as a function of the particular working conditions, state of the rail, measuring speed, resonance of the mechanical and hydraulic circuit for the displacement of the support 1 for example. This adjusting signal Q is amplified by an amplifier 9 the output of which controls a servovalve 10 controlling a double acting jack 11 fast on the one hand with the support 1 and on the other hand with the frame 17 carried by the carriage 18 (see FIGS. 4 and 5) rolling on the rail and carrying the support 1.

Furthermore, a linear displacement sensor 13 connected to a display 14 enables surveying the transverse position of the support 1 with respect to the frame 17 carrying it. This permits a rapid centering of the transducer at the beginning of the work and facilitates the recentering during the work after a loss of contact of the transducer. A video screen 15 enables following the good working of the regulating loop and of its different elements.

Figure 4:
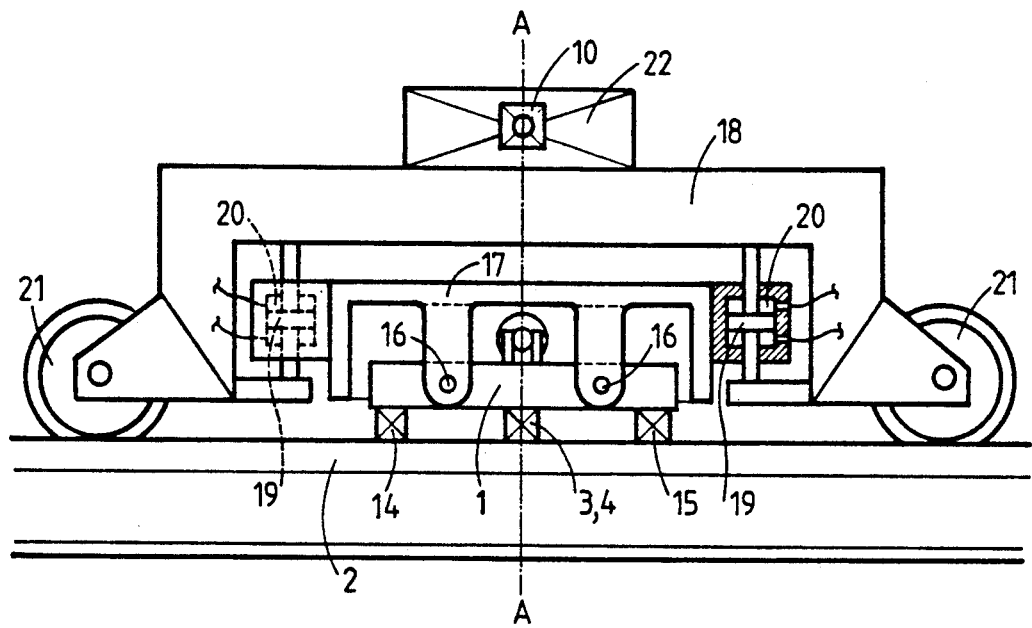
FIG. 4 is a lateral view of a transducer carrying carriage provided with the transverse positioning device according to the invention.
Figure 5:
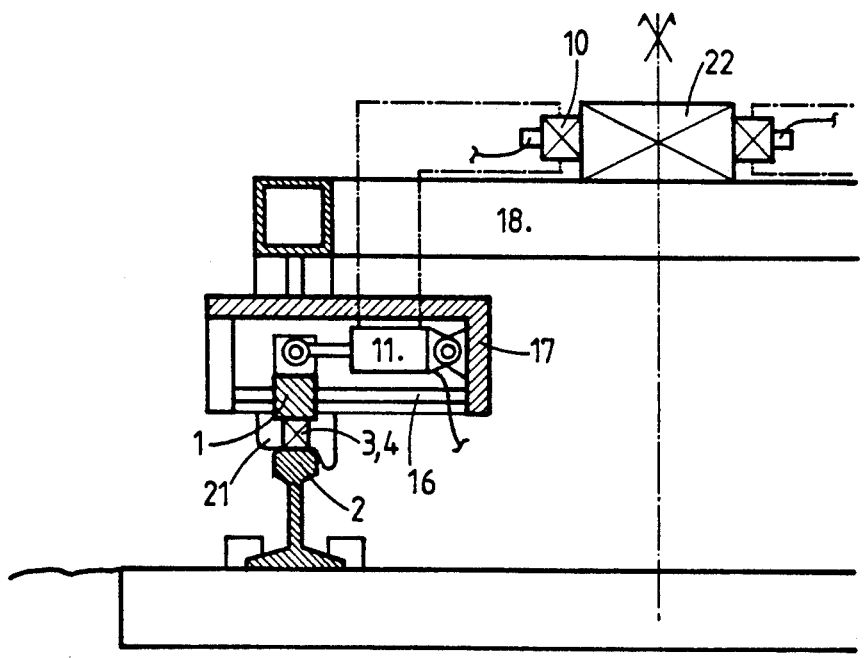
FIG. 5 is a cross-section along line A-A of FIG. 4.

FIGS. 4 and 5 show schematically a particular embodiment of the precise positioning device of ultrasound testing transducers of a laid rail or of a rail in a workshop according to the invention. The support 1 carries a control transducer 3, 4, formed as above of two emitter-receiver transducers forming an angle between them, as well as the testing transducers 14, 15 of the rail. This support 1 is slidingly mounted on rods 16 located along a direction perpendicular to the symmetry plane T of the rail 2 and mounted on a frame 17 displaceable in height with respect to a guiding carriage 18 by means of two double effect jacks 19, 20. The guiding carriage 18 is provided with flanged rollers 21 rolling on the rail 2.

The jack 11 which comprises the linear displacement sensor 13 controlled by the servo-valve 10 enables displacing the support 1 along the rods 16. A casing 22 fast with the carriage 18 houses the electronic part and the feeding of fluid under pressure of the device shown in FIG. 6, the survey shield 15 and the display 14 being placed in the driving cabin of a railroad vehicle through which the carriage 18 is pulled along the railway track.

Numerous variants for the mechanical realizations of such a device are of course realizable without departing the scope of the claimed protection and the spirit of the invention and of the regulating method described. Particularly the support 1 could carry mechanical feelers for measuring the longitudinal or transverse profile of the rail, reprofiling tools or any other element which for its good working has to be positioned precisely transversely with respect to the rail.

As said before, the invention is usable as well on a laid track as in a repair workshop.

I claim:

1. Method for positioning a member displaced along a rail of a railway track transversely with respect to the symmetry plane of said rail, comprising emitting through the head of the rail two diverging ultrasound beams practically perpendicular each to a respective one of the fish plates of said rail, receiving the echoes of these beams reflected by the said fish plates; forming a regulating signal which is a function of the time difference between the emission and the reception of tis echo for each of said two ultrasound beams, using this regulating signal to elaborate a control signal, and using this control signal to control the transverse positioning of the said member.

2. Method according to claim 1, and comparing the signal which is proportional to the time difference between the emission and the reception of the echoes of the two beams to a reference value to form the control signal.

3. Method according to claim 1, wherein a control signal is delivered only is the regulating signal or its comparison with a reference value is greater than a predetermined threshold.

4. Method according to claim 1, wherein said member is at least one ultrasound testing transducer for the rail.

5. Method according to claim 1, wherein each ultrasound wave beam is formed of a pulse train.

6. Method according to claim 5, wherein the ultrasound pulse trains are synchronized.

7. Device for positioning a member displaced along a rail of a railway track transversely with respect to the symmetry plane of said rail, which comprises a guiding carriage rolling on the rail provided with a support, displaceable transversely with respect to the longitudinal axis of the rail, carrying a control transducer in sonic contact with the rail; means for displacing the support in its transverse movements; the control transducer comprising two emitter-receiver transducers forming an angle between them, in sonic contact with the rail, emitting diverging beams of ultrasounds through the head of the rail practically perpendicularly to the fish plates by which they are reflected as echoes received by the said emitter-receiver transducer; and a regulating loop controlling the means for displacing the support in response to a signal which is function of the travelling time difference separating the emission from the reception of the two ultrasound beams.

8. Device according to claim 7, wherein the support carries ultrasound transducers for testing the rail.

9. Device according to claim 7, wherein the regulating loop comprises a comparator delivering a signal corresponding to the difference of travelling times ($\Delta t$) feeding an adder introducing a reference value and delivering a control signal [$f(x)+\Delta t$].

10. Device according to claim 9, wherein the regulating loop comprises further inhibiting means cancelling the control signal as long as its value is less than a pre-established threshold.

* * * * *